United States Patent [19]

Inskip et al.

[11] Patent Number: 4,663,480

[45] Date of Patent: May 5, 1987

[54] INHIBITING POLYMERIZATION OF ETHYLENICALLY UNSATURATED MONOMERS WITH MN(NO$_2$)$_2$

[75] Inventors: Ervin B. Inskip, Troy, Ill.; Douglas C. Caskey, O'Fallon; William E. Dummitt, St. Louis, both of Mo.

[73] Assignee: Mallinckrodt, Inc., St. Louis, Mo.

[21] Appl. No.: 741,383

[22] Filed: Jun. 5, 1985

[51] Int. Cl.$^4$ .............................................. C07C 57/02
[52] U.S. Cl. .......................................... 562/598; 560/4
[58] Field of Search ............................ 562/598; 560/4

[56] References Cited

U.S. PATENT DOCUMENTS

| | | | |
|---|---|---|---|
| 2,607,081 | 4/1951 | Taylor | 560/4 |
| 3,426,063 | 2/1969 | Gros | 260/666.5 |
| 3,987,090 | 10/1976 | Gruber et al. | 560/4 |
| 4,267,091 | 5/1981 | Geelhaar et al. | 526/315 |
| 4,507,495 | 3/1985 | Dougherty et al. | 560/205 |

OTHER PUBLICATIONS

Chem. Abstracts, vol. 81, 171042s (1974), Rao et al., "Radiation Induced Grafting of Acrylic Acid and Methacrylic Acid on to Polyester (Terylene) Fibers", p. 82.

Chem. Abstracts, vol. 83, 117294d (1975), Gaussens et al., "Hydrophobic Substrate With Grafted-On Hydrophilic Coating", p. 185.

*Primary Examiner*—Paul R. Michl
*Assistant Examiner*—Alex H. Walker
*Attorney, Agent, or Firm*—R. G. Jackson; L. N. Goodwin; R. J. Klostermann

[57] ABSTRACT

Disclosed is a process for inhibiting polymerization of polymerizable ethylenically unsaturated monomers such as hydrocarbons, acids and esters, wherein manganese nitrite, i.e. Mn(NO$_2$)$_2$, is employed as an inhibitor. A composition including a polymerizable ethylenically unsaturated monomer and Mn(NO$_2$)$_2$ is also disclosed. In two preferred embodiments, acrylic acid and styrene, respectively, are the monomers.

12 Claims, No Drawings

INHIBITING POLYMERIZATION OF ETHYLENICALLY UNSATURATED MONOMERS WITH MN(NO₂)₂

This invention relates to a process for inhibiting polymerization of polymerizable ethylenically unsaturated monomers such as hydrocarbons, acids and esters, wherein manganese nitrite, i.e. Mn(NO$_2$)$_2$, is employed as an inhibitor. The invention also relates to a composition including a polymerizable ethylenically unsaturated monomer and manganese nitrite.

Polymerizable ethylenically unsaturated monomers such as hydrocarbons, acids and esters undesirably polymerize at various stages of their manufacture, processing, handling, storage and use. A particularly troublesome problem is equipment fouling caused by polymerization in the purification stages of monomer production processes. Polymerization, such as thermal polymerization, during the purification of monomers results in the loss of monomeric material and in loss of production efficiency because the polymer often deposits in or on equipment in contact with the monomers and must be removed at frequent intervals.

A wide variety of substances have been proposed heretofore for inhibiting uncontrolled polymerization, e.g., thermal polymerization, of the above ethylenically unsaturated monomers. However, the heretofore proposed substances have not been entirely satisfactory. Accordingly, there is a substantial need in the art for improved processes for inhibiting polymerization of such monomers.

DESCRIPTION OF THE INVENTION

It has now unexpectedly been found that manganese nitrite, i.e. Mn(NO$_2$)$_2$, effectively inhibits undesired polymerization of ethylenically unsaturated monomers such as unsaturated hydrocarbons, hydrocarbyl acids and hydrocarbyl esters.

Generally stated, in one aspect of the present invention there is provided a process for inhibiting polymerization of a polymerizable ethylenically unsaturated monomer selected from the group consisting of polymerizable ethylenically unsaturated hydrocarbons, polymerizable ethylenically unsaturated acids and polymerizable ethylenically unsaturated esters, which comprises admixing there manganese nitrite in an amount effective for inhibiting polymerization, e.g. thermal polymerization, of the monomer. In general, such amount may be for example from about 0.001 to about 0.05 part by weight per 100 parts by weight of the monomer.

In another aspect, generally stated this invention provides a composition comprising a mixture of the above ethylenically unsaturated monomer and Mn(NO$_2$)$_2$ in an amount effective for inhibiting thermal polymerization of the monomer. The composition of the invention may be stored, handled, used as monomeric material in polymerization processes, and otherwise process with continuing inhibition of thermal polymerization therein.

DETAILED DESCRIPTION OF THE INVENTION AND OF THE MANNER AND PROCESS OF MAKING AND USING IT

Mn(NO$_2$)$_2$ is a known compound which can be prepared as described in any of the following references, which are incorporated herein in pertinent part by reference: (1) Journal of the American Chemical Society, A, 1967, 612-615; (2) Inorganic Chemistry, 6, (1967), 813; and (3) L'Industria Chimica, (May 1932), 577-582, C. Montemartini and E. Vernazza. The Mn(NO$_2$)$_2$ employed in this invention is preferably prepared by the matathesis reaction between AgNO$_2$ and MnBr$_2$.2H$_2$O. Briefly stated, this is effected by adding to a solution of the manganese bromide dihydrate in an alcohol, e.g. ethanol, a solution of silver nitrite in an alcohol, e.g. ethanol, with stirring at about 20° to about 25° C. Ethanol is preferred, and where employed, the resulting AgBr, which is essentially insoluble in ethanol, is then removed by well-known solid-liquid separation procedures, preferably filtration, to provide an ethanol solution of Mn(NO$_2$)$_2$.

Reference (3) above describes conditions under which manganese nitrite and/or solutions thereof are unstable. In general, as reported therein and/or as consequences of the reported information:

(i) Solutions of manganese nitrite are unstable to free-oxygen containing gases such as air and oxygen per se. Such solutions are preferably blanketed under an inert atmosphere, e.g. CO$_2$ or N$_2$ to enhance stability.

(ii) Such solutions are unstable to heat. At elevated temperatures, e.g. above about 20°-25° C., the contained manganese nitrite spontaneously decomposes with evolution of oxides of nitrogen. Stability is generally enhanced by maintaining such solutions at or below room temperature, e.g. about 10°-15° C.

(iii) Such solutions are unstable to strong acids, such as sulfuric acid.

(iv) Hot water (e.g. water at a temperature of about 60° C. or more causes relatively fast decomposition of manganese nitrite.

(v) Solid dry manganese nitrite is relatively stable to air contact, at least for several days. It is best to store and use it under an oxygen-free atmosphere.

In general, in adding manganes nitrite to, or otherwise admixing it with, the monomer composition to be inhibited, it is preferably employed as a solution thereof in an alcohol, e.g. methanol and preferably ethanol, at room temperature, i.e. about 20°-30° C., and preferably under an inert atmosphere (preferably dry nitrogen), and preferably under at least substantially anhydrous conditions.

By empolying manganese nitrite in accordance with this invention, undesired polymerization, such as thermal polymerization, may be inhibited in a wide variety of polymerizable ethylenically unsaturated hydrocarbons, acids and esters. Polymerizable ethylenically unsaturated hydrocarbons which may be employed in this invention include olefins in general, especially alpha olefins containing about 2-20 carbon atoms and preferably 2-8 carbon atoms and conjugated di-olefins, preferably those containing 4-6 carbon atoms such as butadiene, isoprene, and 2,3-dimethyl butadiene, and aromatic hydrocarbons having one or more side chains with ethylenic unsaturation contining, for example, 2-8 carbon atoms.

Suitable ethylenically unsaturated aromatic hydrocarbons include styrene, alpha vinylnaphthalene and p-divinyl benzene.

Suitable ethylenically unsaturated acids include acrylic acid and methacrylic acid. Suitable ethylenically unsaturated esters include the acrylates such as aklyl esters of acrylic acid and an alkanol having from one to about 8 carbon atoms and alkyl esters of methacrylic acid and an alkanol having from one to about 8 carbon atoms.

The acrylate esters advantageously may be an acrylic acid ester of methyl, ethyl, butyl or 2-ethylhexyl alcohol or a methacrylic acid ester of such alcohols.

Mixtures of the above ethylenically unsaturated monomers may be employed. For example, styrene may be admixed in any desired ratio with butadiene or p-divinyl benzene and thermal polymerization inhibited therein in accordance with the invention. It is understood that the above polymerizable ethylenically unsaturated hydrocarbons, acids and esters are merely given as examples of monomers for use in practicing the present invention, and that other suitable ethylenically unsaturated hydrocarbons, acids and esters may be used.

Preferably, the monomer to be inhibited or the composition containing it is a solvent for $Mn(NO_2)_2$; however, this is not necessary for acceptable results. Advantageously, $Mn(NO_2)_2$ is soluble in a wide variety of organic materials, including alcohols, e.g. methanol and ethanol; toluene; dimethylformamide; methylisobutylketone; many of the ethylenically unsaturated monomers, for example, acrylic and methacrylic acid, acrylate and methacrylate esters such as ethyl acrylate and methyl methacrylate; styrene; butadiene and p-divinylbenzene. Accordingly, $Mn(NO_2)_2$ may be dissolved in the monomer to be inhibited for effecting the inhibition without requiring use of water, which is often required in practice as a carrier for other inhibitors such as the ammonium salt of N-nitrosophenylhydroxylamine. This renders the inhibitor complexes especially attractive for addition to acrylic and methacrylic acid and their esters in the final stages of recovery of such monomers in industrial processes for polymerization thereof. Addition of water is undesirable at such stages.

Manganese nitrite may be mixed with a monomer to be inhibited in any suitable manner, including for example, mixing $Mn(NO_2)_2$ with a solid monomer, dissolving it alone in a liqud monomer or forming a solution of it in a solubilizing amount of a solvent therefor, which may be a small quantity of the monomer, and adding the resulting solution to a quantity of the monomer to be inhibited. Monomer-$Mn(NO_2)_2$ mixtures may also be formed by forming the $Mn(NO_2)_2$ in situ in the the monomer, for example by admixing stoichoimetric amounts of a manganese salt such as manganese bromide dihydrate, $MnBr_2.2H_2O$, and a nitrite salt such as silver nitrite with the monomer.

For inhibiting polymerization in monomer purification stages of industrial production processes, the complex advantageously and preferably is first dissolved in a small quantity of a solvent therefor which is the same as the monomer to be inhibited or compatible therewith. The resulting inhibitor solution is then dissolved in the in-process stream containing the monomer to be inhibited.

Advantageously, $Mn(NO_2)_2$ inhibits polymerization of the monomers in both the liquid and vapor phases thereof. This two-phase effectiveness of $Mn(NO_2)_2$ constitutes a significant advantage over the performance of heretofore known inhibitors in ethylenically unsaturated monomers.

While not intending to be bound by any theory of operation, it is believed that $Mn(NO_2)_2$ minimizes or eliminates formation of polymerization initiating agents which often are formed in situ in ethylenically unsaturated monomers under a variety of conditions, including for example, the conditions encountered in a variety of industrial monomer recovery processes.

Manganese nitrite is introduced into the monomer in an amount effective to reduce the rate of formation of undesirable polymer due to unactivated or uncatalyzed polymerization, including the rate of thermal polymerization, and the quantity may vary over wide ranges. In most instances there is no upper limit except as dictated by economics and the practical aspects. The lower limit may vary somewhat depending upon the specific monomer employed. It is understood that the inhibitor need be added only in a small amount which is effective to reduce polymerization, such as thermal polymerization. For example, often 0.001 part to 0.005 part by weight of the inhibitor for each 100 parts by weight of monomer present gives very noticeable improvement. Usually, it is not practical to employ amounts greater than 0.1 part by weight for each 100 parts by weight of monomer, but when desired, larger amounts may be employed such as 0.2 part to 0.5 part by weight or more. About 0.005–0.1 part by weight and preferably about 0.01–0.05 part by weight of the inhibitor for each 100 parts by weight of monomer gives excellent results, but often about 0.01–0.02 part by weight of the inhibitor is the most practical level.

The present invention is further illustrated by the following non-limiting examples. All parts, percentages and other amounts given throughout this disclosure are by weight unless otherwise indicated.

EXAMPLES 1-3

These examples illustrate the use of $Mn(NO_2)_2$ as a polymerization inhibitor for acrylic acid and its comparative effectiveness with the ammonium salt of N-nitrosophenylhydroxylamine (NPH) and phenothiazine (PTZ).

Six polymerization bottles (60 ml. capacity) were each charged with 15 ml. relatively fresh acrylic acid monomer. Ten micromoles of either $Mn(NO_2)_2$, NPH or PTZ were then added to each of two of the bottles with stirring.

The bottles were either sealed in the presence of air or sealed after a nitrogen sparge. Then the bottles were placed in oil bath maintained at the indicated elevated temperature. The heated bottles were observed at frequent intervals and the time for maximum visible thickening of the acrylic acid was noted. The data thus obtained are recorded in Table I. The acrylic acid in each example contained 200 parts per million of the monomethyl ether of hydroquinone, which was incorporated by the supplier and could not safely be removed.

TABLE I

| Ex. | System | In | 100° C.(*) |
|---|---|---|---|
| — | Control (MEHO) | Air | 1 hr. |
| 1 | $Mn(NO_2)_2$ | $N_2$ | 205 |
|  |  | Air | 20 |
| 2 | NPH(**) | $N_2$ | >200 |
|  |  | Air | 3 |
| 3 | Phenothiazine | $N_2$ | 10 |
|  |  | Air | 37 |

(*)Time required for polymerization to occur - in hours
(**)Ammonium salt of N—nitrosophenylhydroxylamine
NOTE: The term "MEHQ" means monomethyl ether of hydroquinone. The data for the control is representative and was not concurrently generated with the data for Examples 1-3.

EXAMPLES 4-6

Vapor Phase Test(s)—Acrylic Acid

Vapor phase inhibition of growth of popcorn polymer was determined using a system containing an oil-bath heated 1-liter round bottom flask equipped with a Vigreux column and provided with a vacuum source and a magnetic stirring device. A liquid mixture formed by adding, with stirring, to one hundred ml of acrylic acid, 100 parts per million (ppm) parts (of the acrylic acid) of manganese nitrite was added to the flask. A stainless steel mesh basket containing as accurately weighed kernel of styrene-butadiene rubber popcorn (0.01 to 0.02 gram) was suspended in the vapor phase above the liquid mixture. The liquid mixture was stirred and heated under reduced pressure. Reflux into the Vigreux column at a reduced pressure of about 50 mm Hg and a bath temperature of 90° C. was carried out for 6 hours. At the end of this time the popcorn kernel was recovered, dried and weighed and the percent change in popcorn kernel weight was calculated. No increase in weight of the kernel indicates complete inhibition of the growth of popcorn polymer in the vapor phase. Additional $Mn(NO_2)_2$ was added incrementally to the mixture during reflux (after each hour thereof, 100 ppm of $Mn(NO_2)_2$ was added).

The above procedure was repeated in two additional tests in which the $Mn(NO_2)_2$ was replaced by isoamyl nitrite and sodium nitrite, respectively, for comparison.

After the 6-hour reflux for each test, the test mixtures were observed for the amount, if any, of polymer in the liquid. Results of the tests are given in the following Table II.

TABLE II

| Ex. | Inhibitor | % Growth | Polymer in Liquid |
|---|---|---|---|
| 4 | $Mn(NO_2)_2$ | +55 | Small amount |
| 5 | Isoamyl nitrite | +464 | Large amount |
| 6 | Sodium nitrite | +155 | Large amount |

EXAMPLES 7-9

Styrene

The procedure of Examples 1-3 was substantially repeated except that 25 ml. of styrene was used in lieu of acrylic acid as the monomer; substances heretofore used for inhibiting styrene polymerization, viz. 2,4-dinitrophenol and 2,4-dinitro-o-cresol, were used for comparative purposes; the various mixtures of styrene and additive were incubated at 95° C. for 6 hours under nitrogen; and each additive was tested at two concentrations in the styrene, viz. 100 ppm and 500 ppm. At the end of the incubation period, the amount of polymer which had formed in each system was determined by gravimetric analysis. The results are set forth in Table III below, wherein "% Polymer" is percent by weight based on the total weight of styrene monomer employed in the test.

TABLE III

| Ex. | Inhibitor | Concentration | % Polymer |
|---|---|---|---|
| 7 | $Mn(NO_2)_2$ | 100 ppm | 0.71% |
|   |   | 500 ppm | 0.09% |
| 8 | 2,4-dinitrophenol | 100 ppm | 2.3% |
|   |   | 500 ppm | 0.3% |
| 9 | 4,6-dinitro-o-cresol | 100 ppm | 7.2% |

TABLE III-continued

| Ex. | Inhibitor | Concentration | % Polymer |
|---|---|---|---|
|   |   | 500 ppm | 0.4% |

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A process for inhibiting polymerization of a polymerizable ethylenically unsaturated monomer selected from the group consisting of polymerizable ethylenically unsaturated hydrocarbons, polymerizable ethylenically unsaturated acids and polymerizable ethylenically unsaturated esters, which comprises admixing therewith a polymerization-inhibiting effective amount of manganese nitrite.

2. The process of claim 1 wherein said amount is from about 0.001 to about 0.5 part by weight per 100 parts by weight of said monomer.

3. The process of claim 1 wherein said monomer is an acrylic monomer selected from the group consisting of acrylic acid, methacrylic acid, alkyl esters of acrylic acid and an alkanol having from one to about 8 carbon atoms and alkyl esters of methacrylic acid and an alkanol having from one to about 8 carbon atoms.

4. The process of claim 1 wherein said monomer is selected from the group consisting of the acrylic acid esters of alcohols selected from the group consisting of methyl, ethyl, butyl and 2-ethylhexyl alcohol and the methacrylic acid esters of said alcohols.

5. The process of claim 1 wherein said monomer is acrylic acid.

6. The process of claim 1 wherein said monomer is styrene.

7. A composition comprising a mixture of a polymerizable ethylenically unsaturated monomer selected from the group consisting of polymerizable ethylenically unsaturated hydrocarbons, polymerizable ethylenically unsaturated acids and polymerizable ethylenically unsaturated esters, and a polymerization-inhibiting amount of manganese nitrite.

8. The composition of claim 7 wherein said amount is from about 0.001 to about 0.5 part by weight per 100 parts by weight of said monomer.

9. The composition of claim 7 wherein said monomer is an acrylic monomer selected from the group consisting of acrylic acid, methacrylic acid, alkyl esters of acrylic acid and an alkanol having fron one to about 8 carbon atoms and alkyl esters of methacrylic acid and an alkanol having from one to about 8 carbon atoms.

10. The composition of claim 7 wherein said monomer is selected from the group consisting of the acrylic acid esters of alcohols selected from the group consisting of methyl, ethyl, butyl and 2-ethylhexyl alcohol and the methacrylic acid esters of said alcohols.

11. The composition of claim 7 wherein said monomer is acrylic acid.

12. The composition of claim 7 wherein said monomer is styrene.

* * * * *